United States Patent [19]

Lofgren et al.

[11] 4,403,862
[45] Sep. 13, 1983

[54] VISIBILITY MEASURING APPARATUS USING LIGHT CONDUCTORS

[75] Inventors: Folke Lofgren; Sven-Erik Soderstrom, both of Västerås, Sweden

[73] Assignee: Asea Aktiebolag, Västerås, Sweden

[21] Appl. No.: 960,438

[22] Filed: Nov. 13, 1978

[30] Foreign Application Priority Data

Nov. 18, 1977 [SE] Sweden ............................. 7713022

[51] Int. Cl.³ ............................................ G01N 21/00
[52] U.S. Cl. ..................................... 356/437; 250/575; 356/435
[58] Field of Search ............... 356/432, 433, 438, 434, 356/435, 437; 250/564, 565, 573, 574, 575

[56] References Cited

U.S. PATENT DOCUMENTS

| | | | |
|---|---|---|---|
| 2,324,304 | 7/1943 | Katzman | 250/573 |
| 3,392,623 | 7/1968 | Walker et al. | 356/434 |
| 3,838,925 | 10/1974 | Marks | 250/573 |
| 3,899,688 | 8/1975 | Perieres | 250/574 |
| 3,954,342 | 5/1976 | Boeke | 356/438 |
| 3,973,852 | 8/1976 | Moore et al. | 356/438 |
| 4,111,559 | 9/1978 | Smith et al. | 356/437 |

FOREIGN PATENT DOCUMENTS 2513061 9/1975 Fed. Rep. of Germany ...... 356/432

*Primary Examiner*—R. A. Rosenberger
*Attorney, Agent, or Firm*—Watson, Cole, Grindle & Watson

[57] ABSTRACT

In visibility measuring apparatus, a transmitter including at least one transmitter optic for emitting light signals and at least one receiver including at least one receiver optic for receiving the emitted light signals are positioned in a measuring base defined by the distance between the at least one transmitter optic and the at least one receiver optic. A central unit controls the light emitting signals and processes the light signals received from the at least one receiver optic. Signal light conductors interconnect at least some of the transmitter and transmitter optics, the central unit and the transmitter and the receiver optics and the central unit. In a modified embodiment each measuring base may include a separate transmitter optic and a separate receiver optic. Additionally, calibration signals may be transmitted from the central unit to each receiver optic by additional light conductors with separate light conductors for returning a reference signal from each receiver optic to the central unit. Temperature induced variations in the transmission capacity of the signal light conductors can be compensated by using a coil of light conductors in parallel therewith.

4 Claims, 4 Drawing Figures

VISIBILITY MEASURING APPARATUS USING LIGHT CONDUCTORS

BACKGROUND

1. Field of the Invention

The present invention relates to a visibility measuring apparatus, and more particularly to such apparatus using at least one transmitter for emission of light signals, a receiver optic for each measuring base for receiving emitted light signals, and a central unit for controlling the light emission and for processing of the signals received from the receiver optic.

2. Prior Art

A visibility measuring apparatus disclosed in British Patent Specification No. 1,497,214 discloses optical mirrors or prisms reflecting the light signals emitted from a common transmitter to a central unit integrated therewith. The central unit receives and detects the reflected signals and determines the travel delay time of the signal. The distance along which a light signal passes from the transmitter to the receiver located in the central unit for evaluating the signal is twice the measuring base. The measuring base is defined as the distance between the transmitter and the reflecting mirrors or prisms. This means that the light signal arriving at the receiver has been damped to such an extent as to correspond to the amount of free-floating water droplets, other particles, or air pollution present in the measuring base or at the transmitter or receiver, which deteriorates the visibility along a distance equal to twice the measuring base.

The mode of operation of such known visibility measuring means is as follows. If a strong, local bank of mist appears, for example, at the center of the longest measuring base, the measuring means indicates that the visibility range is equal to the distance to the bank of mist, irrespective of the visibility conditions behind the mist. Additionally, local pollution of any of the light-reflecting members may cause incorrect indication of the measured visibility conditions.

SUMMARY OF THE INVENTION

The present invention provides a solution for at least the above-mentioned problems. The basic principle of the invention is that light conductors are used at least for conducting the light signals, intercepted by the external receiver optic, to the receiver in the central unit. In a modified embodiment of the invention, a separate transmitter optic and receiver optic are used for each measuring base in a plurality of measuring bases. In another modified embodiment a light conductor is used between the central unit and each receiver optic for transmission of a calibration signal to the respective receiver optic. A light conductor is also used for returning a reference calibration signal to the central unit from each of the receiver optics. In all of the embodiments a coil of light conductors in parallel with the light-signal transmitting conductors may be used to compensate for variations in transmission capacity because of temperature variations.

BRIEF DESCRIPTION OF THE DRAWINGS

The invention will be described with reference to the accompanying drawings, wherein.

DETAILED DESCRIPTION

Figure 1:
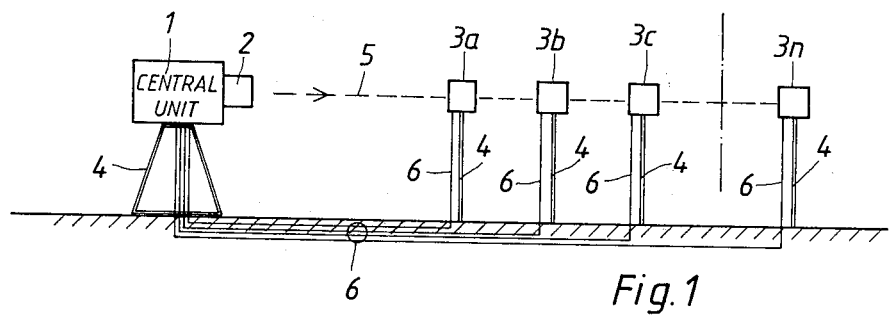
FIG. 1 shows a visibility measuring means with a central transmitter and receiver and a transmitter optic and a receiver optic at each of a number of different measuring base distances from the transmitter.

FIG. 1 shows central unit 1 with transmitter optic 2. Central unit 1 comprises a device for controlling the emission of light pulses from the transmitter and a receiver with a detector for evaluation of the signals arriving from the receiver optics 3a, 3b . . . 3n in a manner known to those skilled in the art. Both central unit 1 and receiver optics 3a–3n are positioned on supports 4 at a certain height above the ground. In the horizontal plane the optics are suitably positioned somewhat laterally displaced, so as not to obscure one another. The light beam from the transmitter optic to the receiver optics is designated 5 in all the Figures. The receiver optics 3a, 3b . . . 3n are arranged to collect the incident light and transmit it to a light conductor 6 through which the light is transmitted to the detector in central unit 1.

In the visibility measuring apparatus in accordance with the invention, the light signal passes the measuring range one time only, namely from transmitter optic 2 to any one of receiver optics 3a, 3b . . . 3n. The light signal travels from the receiver optics to the detector via separate light conductors 6. Since a light conductor 6 has considerably less attenuation than the atmosphere, the light signal arrives with less attenuation than in known visibility measuring apparatus, in which the reflected signal also passes through the atmosphere. Each receiver optic 3a, 3b . . . 3n has its own return light conductor 6 such that the signals arrive at the detector independently of one another.

Since the attenuation in light conductors is known, the actual visibility can be measured by the detector sensing the measuring signal from the receiver optic for each of the different measuring bases.

Figure 2:
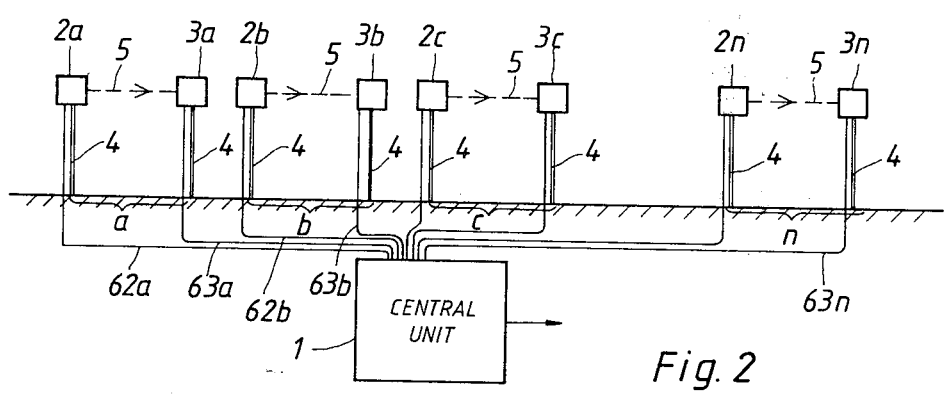
FIG. 2 shows a visibility measuring means with a central transmitter and receiver but having transmitter optics and receiver optics for each measuring base.

The embodiment of the invention shown in FIG. 2 can be used in visibility measuring apparatus to provide a picture of the visibility distribution, for example, along a landing runway. The supervised range is divided into a number of measuring bases a, b, c . . . n and for each measuring base there is arranged a separate transmitter optic 2a, 2b . . . 2n and a separate receiver optic 3a, 3b . . . 3n, respectively. Alternatively, two adjoining measuring bases can be located adjacent to each other such that adjacent transmitter and receiver optics, for example, receiver optic 3a and transmitter optic 2b, can be mounted on the same stand 4, or a couple of adjoining measuring bases can be separated as shown in FIG. 2.

As is clear from FIG. 2, a light conductor passes from central unit 1 to each of the transmitter and the receiver optics. Light conductor 62a thus extends from central unit 1 to transmitter optic 2a, light conductor 63a extends from receiver optic 3a to central unit 1, and so on. By this arrangement, the visibility can be determined along each of the different measuring bases independently of the visibility in any of the other measuring bases. A bank of mist in, for example, measuring base c is not registered in the other measuring bases, as is the case with the device according to FIG. 1. Since the signals emanating from the transmitter in central unit 1 to any of the transmitter optics are light signals, the function of the transmitter optics is to direct the light signal towards the receiver optic corresponding to the respective transmitter optic.

Figure 3:
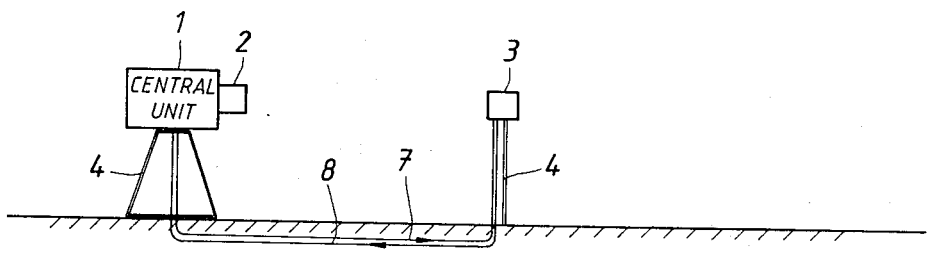
FIG. 3 shows a device for calibration of a receiver optic.

FIG. 3 shows a modification of the invention, which is suitable to use for calibration of conventional visibility measuring apparatus with a separate receiver unit. It can be used in visibility measuring apparatus according to FIGS. 1 and 2. According to the invention, a calibration signal is emitted from transmitter optic 2 through light conductor 7 to receiver optic 3 if a separate receiver is used, or to a receiver optic according to FIGS. 1 and 2. In conventional measuring with a separate receiver, the signal is detected in the normal manner, and in the embodiment according to FIGS. 1 and 2 the signal is conducted to the detector in central unit 1 through second light conductor 8. With such an arrangement, a reference can be obtained from the respective receiver optic without any influence from the visibility conditions prevailing in the atmosphere, or a possible pollution on the incident surface of the receiver optic. Such calibration light conductors are preferably arranged for each receiver or receiver optic.

Figure 4:
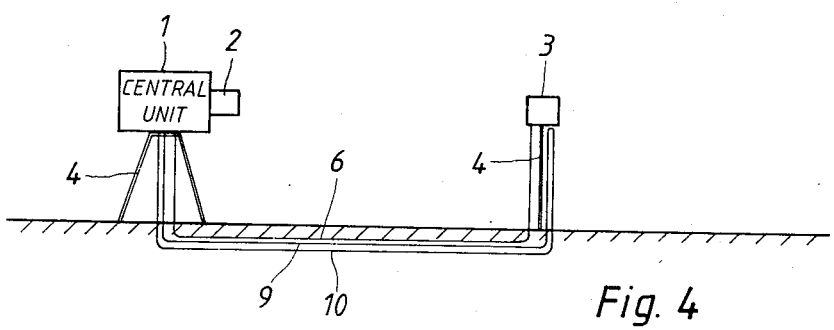
FIG. 4 shows a device for compensation of the temperature dependence of the light-signal optics.

Although the transmission properties of the light conductors are relatively constant, there is a certain temperature dependence of the light attenuation characteristics. It is true that the light conductors are normally laid as cables in the ground where the temperature variations are not too great or fast, but there are certain variations with the times of the year. To compensate for these variations it is possible, as in FIG. 4, to arrange a few additional light conductors 9 and 10 for each receiver or receiver optic. In receiver optic 3 the two light conductors 9, 10 are connected together and the coil thus formed can be used in the detector of central unit 1 as a compensating winding to make up for the variations in the transmitting capacity of the light conductors. Light conductor 6 and compensating winding 9, 10 may, for example, be included as branches in a bridge connection, in which they are allowed to counteract each other. In this arrangement the fact that the compensating winding is twice as long as signal light conductor 6 must be considered.

What is claimed is:

1. Apparatus for measuring atmospheric visibility, comprising:

a plurality of light transmitters located at spaced apart points along a given path;

a corresponding plurality of light receivers, positioned within an area in which the atmospheric visibility is to be measured and each said light receiver being located in spaced relationship to a respective one of said plurality of light transmitters to form a plurality of measuring bases along said path;

control means for generating light pulses and receiving light pulses transmitted through each of said measuring bases independently of light transmitted through any other measuring base;

a plurality of first light conductors for transmitting said light pulses from said control means to respective ones of said plurality of light transmitters;

a plurality of second light conductors for transmitting light pulses from said plurality of light receivers to said control means;

each of said light transmitters including optical means for receiving light pulses from said control means through a respective one of said first light conductors and directing said light pulses towards a corresponding one of said light receivers;

each of said light receivers including optical means for receiving light pulses from a corresponding one of said light transmitters and for directing said light pulses through a respective one of said second light conductors to said control means;

said control means including means for evaluating the light pulses received from said plurality of light receivers to determine visibility along said path; and at least one coil of light conductors extending substantially in closely spaced parallel relationship with at least one of said plurality of first light conductors and at least one of said plurality of second light conductors and connected to said control means for compensating temperature-induced variations in the light transmission capacity of said at least one light conductor and said at least one second light conductor.

2. Apparatus as in claim 1 wherein said evaluating means evaluates the light pulses received from respective ones of said number of light receivers for measuring the light transmission in said measuring bases.

3. Apparatus as in claim 1 or 2 further comprising at least one third light conductor interconnecting said control means and at least one of said plurality of light receivers;

at least one fourth light conductor responsive to the light transmitted by said at least third light conductor for transmitting the same to said control means, said control means further including means for calibrating the light transmitted from said at least one light receiver.

4. Apparatus according to claim 1 or 2 and further comprising at least one calibration light receiver, at least one third light conductor interconnecting said control means and said calibrating light receiver for transmission of a calibration signal from said control means to said calibrating light receiver, at least one fourth light conductor for transmitting the calibrated light from said at least one third light conductor to said control means, and said control means further including means responsive to the transmitted calibration signal for calibrating said calibrating light receiver.

* * * * *